(12) United States Patent
Pironti et al.

(10) Patent No.: US 6,755,965 B2
(45) Date of Patent: Jun. 29, 2004

(54) ETHANE EXTRACTION PROCESS FOR A HYDROCARBON GAS STREAM

(75) Inventors: Filippo Pironti, Caracas (VE); Jorge Vincentelli, Caracas (VE)

(73) Assignee: Inelectra S.A., Caracas (VE)

( * ) Notice: Subject to any disclaimer, the term of this patent is extended or adjusted under 35 U.S.C. 154(b) by 0 days.

(21) Appl. No.: 09/839,759

(22) Filed: Apr. 20, 2001

(65) Prior Publication Data

US 2002/0042550 A1 Apr. 11, 2002

Related U.S. Application Data

(60) Provisional application No. 60/202,401, filed on May 8, 2000.

(51) Int. Cl.$^7$ .............................. B01D 3/00; C10G 7/00; F25J 3/06; F17C 3/10
(52) U.S. Cl. ....................... 208/347; 208/350; 208/351; 208/353; 585/802; 62/622; 62/48.2; 62/631
(58) Field of Search ................................. 208/347, 350, 208/351, 353; 585/802; 62/622, 48.2, 631

(56) References Cited

U.S. PATENT DOCUMENTS

| | | | |
|---|---|---|---|
| 4,278,457 A | 7/1981 | Campbell et al. ............... | 62/24 |
| 4,597,788 A | 7/1986 | Apffel ........................... | 62/26 |
| 4,687,499 A | 8/1987 | Aghili ........................... | 62/24 |
| 4,689,063 A | 8/1987 | Paradowski et al. ............ | 62/28 |
| 4,851,020 A | 7/1989 | Montgomery, IV ............. | 62/24 |
| 4,869,740 A | 9/1989 | Campbell et al. ............... | 62/24 |
| 5,275,005 A | 1/1994 | Campbell et al. ............... | 62/24 |
| 5,568,737 A | 10/1996 | Campbell et al. ............... | 62/621 |
| 5,588,306 A | 12/1996 | Schmidt ........................ | 62/614 |
| 5,890,377 A | 4/1999 | Foglietta ........................ | 62/621 |
| 5,953,935 A | 9/1999 | Sorensen ....................... | 62/621 |
| 6,116,050 A * | 9/2000 | Yao et al. ....................... | 62/630 |
| 6,125,653 A * | 10/2000 | Shu et al. ....................... | 62/622 |

* cited by examiner

*Primary Examiner*—Walter D. Griffin
*Assistant Examiner*—Tam M. Nguyen
(74) *Attorney, Agent, or Firm*—Hoffmann & Baron, LLP

(57) ABSTRACT

A process for ethane extraction from a gas stream based on turboexpansion and fractionation with no mechanical refrigeration is provided. The feed gas is sweetened and dehydrated by a conventional amine process and by a molecular sieve unit, to remove carbon dioxide and water. After this pretreatment, the feed gas undergoes to a series of cooling steps through a cryogenic brazed aluminum heat exchanger and fed to a demethanizer column. A stream rich in methane is recovered from the top of this column and fed to a centrifugal compressor and subsequently routed to a booster/turboexpander. The temperature of the methane gas is greatly reduced by the expansion allowing the cooled methane stream to be a cooling source for cryogenic heat exchanger. Feed for a de-ethanizer column comes from the bottom liquids of the de-methanizer column. Ethane is recovered overhead at the de-ethanizer column.

5 Claims, 2 Drawing Sheets

ETHANE EXTRACTION PROCESS FOR A HYDROCARBON GAS STREAM

CROSS-REFERENCE TO RELATED APPLICATIONS

The present application claims priority to United States Provisional Patent Application Serial No. 60/202,401, filed May 8, 2000, the contents of which are incorporated by reference herein.

FIELD OF THE INVENTION

The present invention relates generally to a method for recovering ethane from a hydrocarbon gas stream. More particularly, the present invention relates to an improved method having turboexpansion of a methane-rich stream to provide refrigeration in an ethane extraction process which is used to recover an ethane product.

BACKGROUND ON THE INVENTION

The production and consumption of ethane is rising because it is a valuable petrochemical feedstock for ethylene manufacture. Furthermore, highly pure methane and propane are also valuable products of an ethane extraction plant.

FIG. 1 is simplified schematic of a typical ethane extraction plant. A hydrocarbon feed, containing methane, ethane, propane and possibly heavier hydrocarbons, is fed to a demethanizer column. The overhead of the demethanizer column is typically a methane-rich stream. The bottom of the demethanizer column is fed to a de-ethanizer column. An ethane-rich stream is recovered overhead and a propane-rich stream is recovered from the bottom of the de-ethanizer column.

The hydrocarbon feed is often cooled through a refrigeration section (not shown) prior to entering the demethanizer column. Refrigeration is a useful technique for achieving low temperatures necessary for the separation of methane from the other hydrocarbon constituents in the hydrocarbon feed.

Several methods currently exist for recovering methane, ethane and propane from hydrocarbon gas streams. Some typical examples of isolating and extracting ethane and or propane are disclosed in U.S. Pat. Nos. 4,278,457; 4,597, 788; 4,689,063; 4,851,020; 4,869,740; 5,275,005; 5,568, 737; 5,588,306; 5,890,377; and 5,953,935.

Existing ethane extraction plants use (i) propane refrigerant as the cooling means for ethane separation or (ii) a combination of turboexpansion and Joule-Thompson expansion of the hydrocarbon feed. The use of turboexpansion on a gas feed to an ethane extraction plant is possible when the gas stream is lean, i.e., having a low concentration of hydrocarbons heavier than methane. When a gas stream is rich in ethane or propane, these hydrocarbons would typically condense into liquids during cooling, resulting in insufficient cooling at the turboexpansion facilities associated with the gas feed.

For a gas stream rich in ethane or propane, however, a propane refrigeration system is commonly used to cool the gas feed stream. Propane refrigeration, however, often becomes inefficient with lean feeds.

A cold methane stream has been used to partially cool the gas feed to an ethane extraction plant. A process disclosed in U.S. Pat. No. 4,687,499 used a cool overhead methane stream from a demethanizer column as a cooling source for a natural gas feed. The cool demethanizer overhead methane stream cooled the natural gas feed in a heat exchanger. The methane stream was then compressed before being recovered as a methane product. This process, however, is limited in overall efficiency because it does not fully utilize the cooling potential of the methane stream.

There is a need for an ethane extraction process capable of efficiently and economically extracting ethane from both lean and rich gas feeds.

SUMMARY OF THE INVENTION

The present invention is a process for recovering ethane from a hydrocarbon gas feed stream containing methane, ethane, propane and possibly heavier hydrocarbons. Cooling of the feed stream is accomplished in an exchanger, such as a cryogenic heat exchanger. Turboexpansion of a methane-rich stream provides a cooling source for the cryogenic heat exchanger to cool the hydrocarbon gas feed.

The cooled hydrocarbon gas feed is separated into a methane-rich stream and an ethane/propane-rich stream in a demethanizer column. An ethane-rich stream is recovered from a de-ethanizer column.

The turboexpansion of a methane-rich streams permits the processing of lean and/or rich hydrocarbon feed streams while avoiding undesirable condensation that may lower cooling capability of the refrigeration system, such as the cryogenic heat exchanger.

In one aspect, the present invention is a method for recovering ethane from a hydrocarbon gas stream having methane, ethane and propane which includes the steps of (i) providing the hydrocarbon gas stream; (ii) cooling the hydrocarbon gas stream by refrigeration to form a cooled hydrocarbon gas stream; (iii) separating the cooled hydrocarbon gas stream into a methane-rich stream and an ethane/propane-rich stream; (iv) expanding the methane-rich stream from a high pressure to a lower pressure to lower the temperature of the methane-rich stream which then provides a cooling source for the refrigeration of the hydrocarbon gas stream; (v) separating the ethane/propane-rich stream into an ethane-rich stream and a propane-rich stream; and (vi) recovering methane-rich, ethane-rich and propane-rich product streams.

Desirably the step of expanding the methane-rich stream includes the steps of (i) compressing the methane-rich stream; (ii) cooling the compressed methane-rich stream; and (iii) turboexpanding this cooled and compressed methane-rich stream.

DETAILED DESCRIPTION OF THE PRESENT INVENTION

The process of the present invention is capable of producing an ethane-rich stream with the following typical, but non-limiting, characteristics:

| | |
|---|---|
| Methane: | 0.5% molar maximum, |
| Ethane: | 96.5% molar minimum, and |
| Propane: | 3% molar maximum. |

The feed for the process of the present invention is a hydrocarbon mixture gas at about 25° C. and about 70 kg/cm²abs. The process of the present invention can recover hydrocarbon products from lean, normal and rich hydrocarbon mixtures. Typical properties of these feeds are shown below in Table I.

TABLE I

Hydrocarbon Feed Compositions

| | mole fraction | | |
|---|---|---|---|
| Composition | Lean | Normal | Rich |
| Nitrogen | 0.0010 | 0.0010 | 0.0010 |
| $CO_2$ | 0.0760 | 0.0760 | 0.0748 |
| Methane ($C_1$) | 0.7338 | 0.6328 | 0.5316 |
| Ethane ($C_2$) | 0.1762 | 0.2700 | 0.3573 |
| Propane ($C_3$) | 0.0130 | 0.0200 | 0.0350 |
| $C_4$ + Hydrocarbons | 0.0000 | 0.0002 | 0.0003 |

The process of the present invention is not limited to the processing of the feeds described above in Table I, but the inventive process can handle a wide range of feed compositions. The above-described values are cited as illustrations of how the invention process performs under different lean and rich hydrocarbon compositions.

Carbon dioxide and water should be removed from the hydrocarbon feed to avoid solid formation (due to freezing of the components) in cold sections of the plant. The cold sections can include refrigeration sections, distillation columns, heat exchangers and other associated equipment operating at conditions that would lead to the freezing of carbon dioxide or water. Carbon dioxide is typically removed from the feed by an amine absorption unit. Water is often removed from the feed by a molecular sieve unit. Desirably the levels of carbon dioxide and water in the feed gas after these treatments are less than about 0.02% and 0.0001% molar, respectively.

Figure 1:
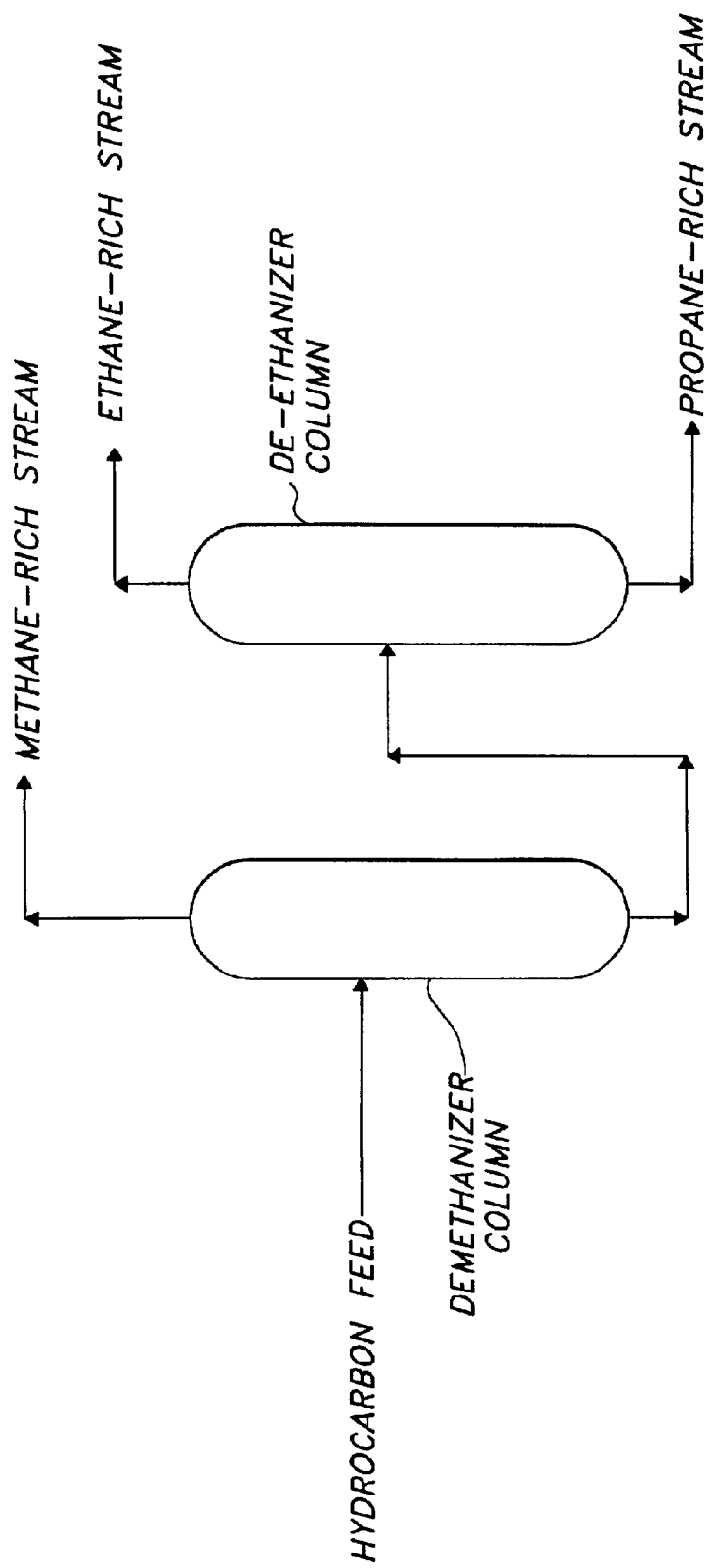
FIG. 1 is simplified flow chart for recovering methane, ethane and propane by distillation of a light hydrocarbon gas feed.
Figure 2:
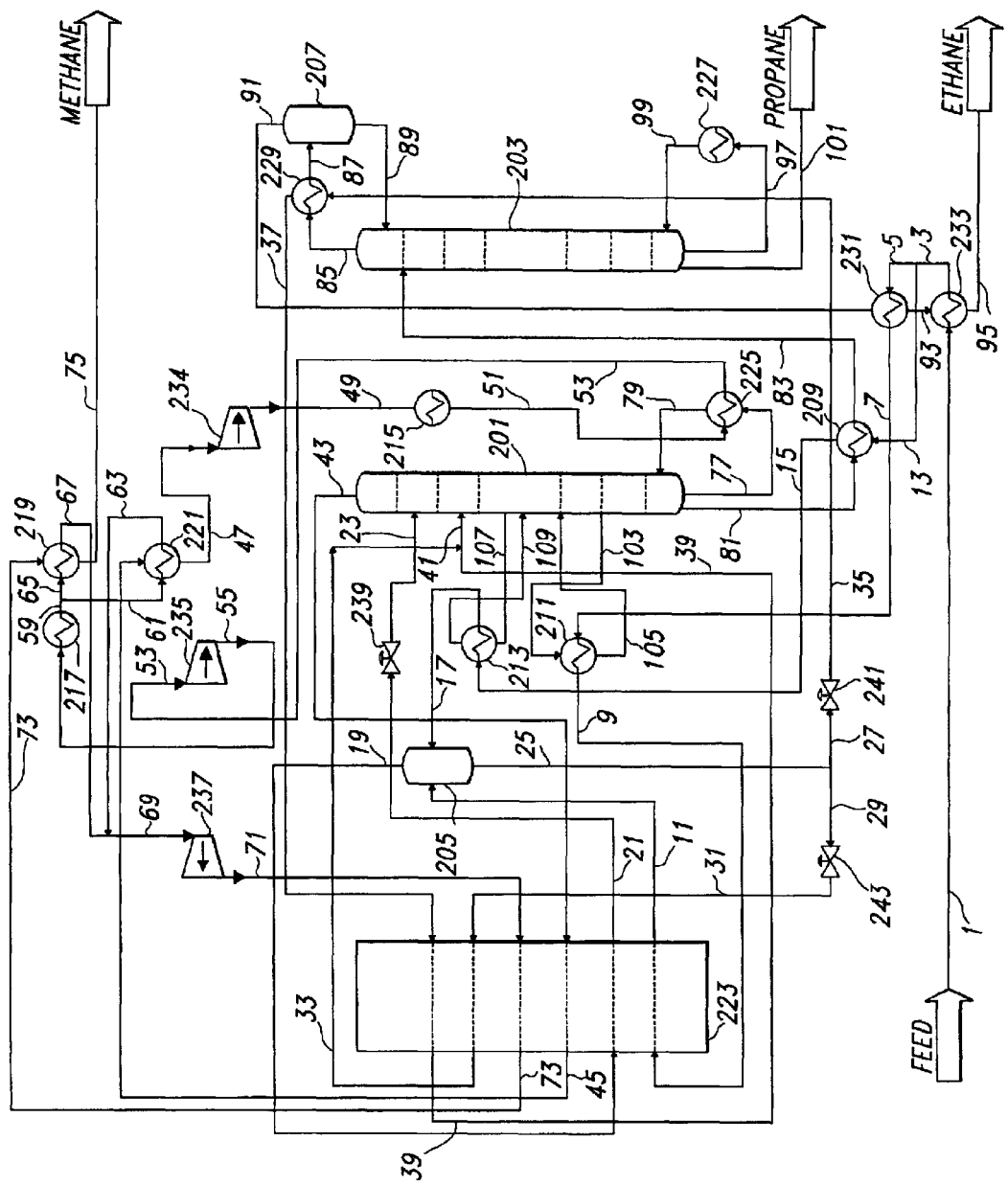
FIG. 2 is a flow chart of the process of the present invention for recovering methane, ethane and propane from a light hydrocarbon stream by distillation and turboexpansion of a methane-rich stream which is used to cool the refrigeration system of the present invention.

FIG. 2 is a schematic flow diagram of the process of the present invention. The hydrocarbon gas feed, which is typically at about 25° C. and about 70 kg/cm²abs, is first sweetened and dehydrated by a conventional amine process (not shown) and by a molecular sieve unit (not shown). The hydrocarbon gas feed is then typically precooled with cooling water at a heat exchanger (not shown).

The precooled hydrocarbon gas feed stream 1 is further cooled at gas—gas economizer 233 to provide a feed stream 3. The feed stream 3 is then divided in two parallel streams 5, 13. The parallel feed stream 5 is cooled in exchanger 231 to about 10° C. by heat exchange with ethane-rich stream 91 to yield a cooled feed stream 7. The ethane-rich stream 91 is at about −6° C. coming out from the top of the de-ethanizer column 203 via heat exchanger 229 and separator 207. The cooled feed stream 7 is further cooled to about −3° C. to provide a further cooled feed stream 9 by supplying heat to one side reboiler 211 of the demethanizer column 201. This further cooled feed stream 9 is passed through a cryogenic heat exchanger 223, which is desirably a cryogenic brazed aluminum heat exchanger. The further cooled feed stream 9 is partially condensed in the cryogenic heat exchanger 223 to yield a partially condensed feed stream 11. The temperature of the partially condensed feed stream 11 is at about −26° C. The partially condensed feed stream 11 is then forwarded to separator 205.

The parallel feed stream 13 is cooled in exchanger 209 to about −6° C. by heat exchange with a substantially liquid stream 81 coming from the bottom of the demethanizer column 201. The cooled feed stream 15 from exchanger 209 is further cooled to about −26° C. by supplying heat to one side of reboiler 213 of the demethanizer column 201 to yield a further cooled feed stream 17. The further cooled feed stream 17 which, is partially condensed, is fed to a separator 205 together with the other partially condensed feed stream 11 coming from the cryogenic heat exchanger 223.

In the separator 205, vapor is separated from condensed liquid. The vapor 19 from the separator 205 is passed through the cryogenic heat exchanger 223 where it is substantially condensed at a temperature of about −89° C. The substantially condensed feed stream 21 from the cryogenic heat exchanger 223 is then expanded through an expansion valve 239 to the operating pressure of the demethanizer column 201 to yield demethanizer feed stream 23.

During expansion, the substantially condensed feed stream 21 is cooled to approximately −94° C. to yield the demethanizer feed stream 23. The demethanizer feed stream 23 is fed to a location near the top of the demethanizer column 201. The reduction of temperature as most gases are expanded is known as the Joule-Thompson effect. Joule-Thompson expansion is a useful technique for lowering the temperature of the hydrocarbon gas streams of the present invention.

The feed liquid 25 from the separator 205 is divided in two feed liquid portions 27, 29. One portion 27 is expanded through an expansion valve 241 where its temperature is reduced to about −57° C. to provide expanded feed stream 35. This expanded feed stream 35 from the expansion valve 241 is used for cooling purposes in the heat exchanger 229 at the overhead of de-ethanizer column 203. The feed stream 37 exiting from exchanger 229 is forwarded to the cryogenic heat exchanger 223 to provide cooling capacity thereat. After providing cooling capacity feed stream 37 exits the cryogenic heat exchanger 223 as stream 39.

The other feed liquid portion 29 is expanded through an expansion valve 243 to provide expanded feed stream 31. The expanded feed stream 31 from expansion valve 243 is then routed to the cryogenic heat exchanger 223 to also provide cooling capacity thereat. Feed stream 33 exits the cryogenic heat exchanger 223 after providing its cooling capacity. Streams 33 and 39 are recombined to form demethanizer feed stream 41. Demethanizer feed stream 41 is fed to the mid-region of the demethanizer column 201, which is below the entry location of demethanizer feed stream 23.

The demethanizer 201 is a reboiled absorber type of column where methane is mainly separated at the top and ethane and heavier hydrocarbons are concentrated in the bottom of the column. The demethanizer column 201 has two side reboilers 211 and 213 and a main thermosyphon reboiler 225 to provide enthalpy to the column.

Demethanizer overhead stream 43 is rich in methane (97.5% molar), and leaves the top of the demethanizer column 201 at about −95° C. The demethanizer overhead stream 43 is routed to the cryogenic heat exchanger 223 where it gives cooling capacity thereat and it is warmed to about −9° C. The methane-rich stream 45 exiting the cryogenic heat exchanger 223 is further warmed to about 25° C. at heat exchanger 221. The methane-rich stream 47 from heat exchanger 221 goes to a first compressor 234, where its temperature increases up to about 114° C. after compression. The compressed methane-rich stream 49 from the first compressor 234 is cooled first with cooling water (not shown) in exchanger 215 and then further cooled by supplying heat to the main reboiler 225 of the demethanizer column 201.

The methane-rich stream 53 from reboiler 225 is at about at 5° C. This methane-rich stream 53 is further compressed in a second booster compressor 235 where its temperature increases up to about 60° C. after compression. The compressed methane-rich gas 55 from the second booster compressor 235 is then cooled with cooling water (not shown) in exchanger 217. The cooled methane-rich stream 59 from exchanger 217 is then divided into parallel streams 61, 65. Stream 65 is cooled in exchanger 219. Stream 61 is cooled in exchanger 221. The cooled streams 63 and 67 from respective exchanges 221 and 219 are recombined to form stream 69, which has a temperature of approximately –7° C. Stream 69 enters a turboexpander 237.

The turboexpander 237 is a work expansion machine in which mechanical energy is extracted from a high-pressure gas, such as stream 69. This machine expands the gas in a substantially isoentropic manner to the pressure of the demethanizer column 201. The work from the expansion drives the booster compressor 235. After expansion, expanded stream 71 exits turboexpander 237 at a temperature of about –96° C. This cooled and expanded stream 71 provides cooling capacity to the cryogenic heat exchanger 223. After providing cooling capacity expanded stream 73 exits cryogenic heat exchanger 223 at about –9° C. The stream 73, which is rich in methane, is further warmed to about 25° C. at heat exchanger 219. The methane-rich stream 75 exiting from heat exchanger 219 is ready for sale. A portion of methane-rich stream 75 (not shown) can be recycled to the compressor 234.

The liquid stream 81 exiting from the bottom of the demethanizer column 201 is at about –3° C. and is mainly ethane, propane and heavier hydrocarbons. The stream 81 is expanded though an expansion valve (not shown), and its temperature is reduced to approximately –6° C. This expanded stream is then used for cooling purposes at exchanger 209. At exchanger 209 the stream 81 is partially vaporized before it is fed as stream 83 to the de-ethanizer column 203.

The de-ethanizer column 203 is a fractionation column with a condenser 229 and a separator 207 arrangement at the column overhead and a thermosyphon reboiler 227 at the column bottoms. The duty of a reboiler 227 may be provided by warm water or other convenient heat source (not shown). The liquid propane-rich stream 101 exiting the bottom of the de-ethanizer column 203 is mainly propane (99% molar). The propane purity of stream 101 depends on, among other things, the amounts of $C_4+$ hydrocarbons present in the hydrocarbon feed stream 1. Stream 101 leaves the de-ethanizer column 203 at about 53° C. The gas stream 85 leaving at the top of the de-ethanizer column 203 is at a temperature of about –6° C. The gas stream 85 is essentially ethane (minimum 96.5% molar). The gas stream 85 is cooled in exchanger 229 to yield gas stream 87. Gas stream 87 is separated into gas stream 91 and liquid stream 89 at separator 207. Gas stream 91 is used as a cold stream for cooling duty at the heat exchangers 231 and 233 before it is sent for storage and delivery purposes as an ethane-rich product stream 95. Liquid stream 89 from the separator 207 is returned to de-ethanizer column 203.

Features of the present invention are further described below in the following examples:

EXAMPLES

Process simulations were performed with the gas feeds shown above in Table I in order to generate the outputs required to analyze and compare the results of the different feeds and different processes. Hysys® version. 2.1.1 from HyProtec is a software package that was used for process simulations. The data from an existing prior art process was used to validate the simulations.

The following parameters were used for technical evaluation:

Ethane Recovery: Ethane recovery is the percentage of ethane product recovered from the feed. The ethane recovery was set at 92% minimum.

Horsepower Consumption: The horsepower requirements are a measure of investment and operating cost associated with major large rotative equipment.

Total Number of Equipments: This factor is a relative measure of operational complexity, investment cost, operating cost and maintenance cost.

Reliability: This factor considers the probability of failure for each process scheme evaluated. The factor is a function of the equipment availability and the system complexity.

Operational Flexibility: This factor considers the capacity of any process scheme to obtain same ethane recovery for lower flow rates and different feed gas composition.

The results of the simulations for the three hydrocarbon feeds described above in Table I are compared below in Table II.

TABLE II

Process Simulations

| Case: Operating Conditions | Units | Lean | Normal | Rich |
| --- | --- | --- | --- | --- |
| Feed Gas Pressure | kg/cm² abs | 68 | 68 | 68 |
| Feed Gas Temperature | ° C. | 26 | 26 | 26 |
| De-methanizer Column Overhead Temperature | ° C. | –98.4 | –94.6 | –84.4 |
| De-methanizer Column Bottom Temperature | ° C. | –1.7 | –1.6 | –0.8 |
| De-methanizer Reboilers Total Duty | MMkcal/h | 2.27 | 1.83 | 1.55 |
| De-ethanizer Vapor Distillate Temperature | ° C. | –5.6 | –5.7 | –5.0 |
| De-ethanizer Condenser Duty | MMkcal/h | 0.020 | 0.014 | 0.011 |
| De-ethanizer Reboiler Duty | MMkcal/h | 0.84 | 1.47 | 1.97 |
| Methane Gas Turboexpander Discharge Temperature | ° C. | –95.0 | –95.9 | –86.1 |
| Ethane Recovery | % | 97.0 | 95.9 | 92.1 |

As shown in Table II, the percentage of ethane recovered with turboexpansion process of the present invention is about 96% for normal gas feed, about 97% for lean gas feed and about 92% for rich gas feed. As the feed becomes leaner, the ethane recovery increases for the process of the present invention. This is an advantage for the turboexpander scheme of the present invention because as the concentration of methane in the feed increases, lower temperatures are achieved as shown in Table II. As a consequence of these lower temperatures, higher ethane recoveries are obtained with the inventive process.

Table III is shown below where the results of the simulations for the normal feed case described above are compared for technical evaluation with an existing prior art plant that uses a propane refrigeration cycle to process the same feed.

TABLE III

Process Comparison

| Scheme Operating Conditions | Units | Propane Refrigeration Process | Methane Stream Turbo-Expansion Process |
|---|---|---|---|
| Feed Gas Pressure | Kg/cm² abs | 68 | 68 |
| Feed Gas Temperature | ° C. | 26 | 26 |
| De-methanizer Column Overhead Temperature | ° C. | −94 | −94.6 |
| De-methanizer Column Bottom Temperature | ° C. | −3 | −1.6 |
| De-methanizer Reboilers Total Duty | MMkcal/h | 1.86 | 1.83 |
| De-ethanizer vapor distillate Temperature | ° C. | −6 | −5.7 |
| De-ethanizer Condenser Duty | MMkcal/h | 0.67 | 0.014 |
| De-ethanizer Reboiler Duty | MMkcal/h | 1.17 | 1.47 |
| Propane Lowest Refrigeration Temperature | ° C. | −33 | Not Present |
| Methane Gas Compressor Discharge Pressure | kg/cm2 abs | Not present | Present |
| Booster Compressor Discharge Pressure | kg/cm2 abs | Not present | Present |
| Methane Gas Turboexpander Discharge Temperature | ° C. | Not present | −96 |

As shown above in Table 3, both schemes have approximately similar operating temperatures and duties for the demethanizer and de-ethanizer columns. One significant difference between the processes is the source of the cooling capacity.

A performance chart is shown below in Table 4 where both schemes are compared for a feed gas flow rate of 80 t/h and 56 t/h, or operating at 100% and 70% of capacity, respectively.

TABLE IV

Comparison at Different Plant Capacities

| Case | Propane Refrigeration Process | | Methane Stream Turboexpansion Process | |
|---|---|---|---|---|
| Performances | 100% Capacity | 70% Capacity | 100% Capacity | 70% Capacity |
| Ethane Recovery | 95 | 95 | 95.9 | 97 |
| Methane Gas Compressor Power | Not Present | Not Present | 2713 HP | 2713 HP |
| Propane Compressor Power | 2150 HP | 2150 HP | Not Present | Not Present |
| Total Compression Power | 2150 HP | 2150 HP | 2713 HP | 2713 HP |
| Cryogenic Exchanger, UA | 1.82 MMkcal/h° C. | 1.82 MMkcal/h° C. | 1.03 MMkcal/h° C. | 1.03 MMkcal/h° C. |
| Total Number of Equipments | 20 | 20 | 13 | 13 |

As shown above in Table IV, the ethane recovery achieved with the turboexpansion process of the present invention is greater than that achieved with propane refrigeration, both at 100% capacity and at 70% capacity. At the turndown operation of 70% capacity, the ethane recovery increases for the turboexpansion method. The horse power consumption for the turboexpansion scheme is about 25% greater than the consumption with the refrigeration scheme. The number of equipments in the turboexpansion case is 35% lower than that for the refrigeration process. The UA of the cryogenic heat exchanger is about 75% larger for propane refrigeration scheme.

The percentage of ethane recovered with turboexpansion process of the present invention is about 96% for the normal feed, about 97% for the lean feed and about 92% for the rich feed. The ethane recovery achieved with the turboexpansion process is greater than that achieved with propane refrigeration process, both at 100% capacity and at 70% capacity. At turndown operation, the recovery of ethane increases for the process of the present invention. The horse power consumption for the turboexpansion process is about 25% greater than the consumption of the propane refrigeration process. The number of equipments in the turboexpansion case, however, is 35% lower than that for the refrigeration process.

Various changes to the foregoing described and shown process would now be evident to those skilled in the art. Accordingly, the particularly disclosed scope of the invention is set forth in the following claims.

What is claimed:

1. A process for recovering ethane from a methane, ethane and propane containing gas stream comprising:
   (a) providing the hydrocarbon gas stream comprising from about 50% to about 75% by mole methane, from about 15% to about 40% by mole ethane and from about 1% to about 4% by mole propane;
   (b) cooling the hydrocarbon gas stream to provide a partially condensed feed stream;
   (c) separating said partially condensed feed stream into a vapor hydrocarbon feed stream and a condensed liquid hydrocarbon feed stream;
   (d) providing a cryogenic heat exchanger;
   (e) cooling the vapor hydrocarbon feed stream in a the cryogenic heat exchanger by heat exchange with a first cooling source, a second cooling source and a third cooling source to form a cooled and substantially condensed hydrocarbon feed stream, wherein said first cooling source is said condensed liquid hydrocarbon feed stream;
   (f) distilling said cooled and substantially condensed hydrocarbon feed stream and said condensed liquid hydrocarbon feed stream in a demethanizer column to form a methane-rich stream and an ethane/propane-rich stream, wherein said methane-rich stream is said second cooling source;
   (g) compressing said methane-rich stream to form a compressed methane-rich stream;
   (h) cooling said compressed methane-rich stream to form a compressed methane-rich stream;

(i) turboexpanding said compressed methane-rich stream to a lower pressure to provide said third cooling source for said cryogenic heat exchanger;

(j) distilling said ethane/propane-rich stream in a de-ethanizer column to form an ethane-rich stream and a propane-rich stream; and (k) recovering said ethane-rich stream.

2. The process of claim 1 wherein said ethane-rich stream contains at least 90% by mole ethane.

3. The process of claim 1 wherein said ethane-rich stream contains less than about 0.5% by mole methane and less than about 3% by mole propane.

4. The process of claim 1 wherein said methane-rich stream contains at least 95% by mole methane.

5. The process of claim 1 wherein said ethane-rich stream contains at least 96.5% by mole ethane.

* * * * *